United States Patent [19]
Gould et al.

[11] Patent Number: 5,846,739
[45] Date of Patent: *Dec. 8, 1998

[54] IMMUNOHISTOCHEMICAL DETECTION ASSAY FOR CARCINOMA PROLIFERATIVE STATUS

[75] Inventors: Michael N. Gould, Madison, Wis.; Steven P. Stoesz, Morristown, N.J.

[73] Assignee: Wisconsin Alumni Research Foundation, Madison, Wis.

[*] Notice: The term of this patent shall not extend beyond the expiration date of Pat. No. 5,627,034.

[21] Appl. No.: 779,870

[22] Filed: Jan. 6, 1997

Related U.S. Application Data

[63] Continuation-in-part of Ser. No. 567,509, Dec. 5, 1995, Pat. No. 5,627,034.

[51] Int. Cl.$^6$ ..................... G01N 33/567; G01N 33/574; G01N 33/53; C07K 16/00
[52] U.S. Cl. .................... 435/7.1; 435/7.21; 435/7.23; 435/7.7; 435/7.72; 435/7.8; 435/7.9; 435/7.91; 435/7.92; 435/40.52; 435/40.51; 435/40.5; 530/387.1; 530/350; 530/387.7
[58] Field of Search .................... 435/7.23, 6; 536/24.3, 536/24.31, 22.1; 530/380

[56] References Cited

PUBLICATIONS

Abstract of S. Stoesz et al. "Overexpression of neu-related lipocalin (NRL) in neu-initiated but not ras or chemically initiated rat mammary carcinomas", Chemical Abstracts + Indexes, vol. 5, No. 124, 29 Jan. 1996, p. 870.

Abstract of S. Stoesz et al. "Indentification of a Lipocalin Uniquely Overexpressed in Neu-Initiated Rat Mammary Carcinomas", Proceedings of the Annual Meeting of the American Association for Cancer Research, San Francisco, Apr.10–13. 1994, p. 150.

L. Kjeldsen et al., "Characterization of two ELISAs for NGAL, a newly described lipocalin in human neutrophils", 2 J. Immuno. Meth. 155–164 (Nov. 13, 1996).

S. Bartsch, et al., Cloning And Expression Of Human Neutrophil Lipocalin cDNA Derived From Bone Marrow And Ovarian Cancer Cells, 357 FEBS Letters 255–259 (1995).

J. Bundgaard, et al., Molecular Cloning And Expression Of A cDNA Encoding NGAL A Lipocalin Expressed in Human Neutrophils, 202 Biochem. & Biophy. Res. Comm. 1468–1475 (1994).

L. Kjeldsen, et al., Isolation And Primary Structure Of NGAL, A Novel Protein Associated With Human Neutrophil Gelantinase, 268 J. Bio. Chem. 10425–10432 (1993).

S. Stoesz, et al., Isolation Of A Lipocalin Uniquely Overexpressed In Neu–Initiated Rat Mammary, AACR Abstract (1994).

S. Stoesz, et al., Cloning Of Genes Overexpressed In Neu–Initiated Rat Mammary Tumors, AACR Abstract (1992).

S. Xu, et al., The Development Of An Assay For Human Neutrophil Lipocalin (HNL)–To Be Used As A Specific Marker Of Neutrophil Activity In Vivo And Vitro, 171 J. Immu. 245–252 (1994).

N. L. Petrakis, Nipple Aspirate Fluid In Epidemiologic Studies Of Breast Disease, 15 Epid. Rev. 188–195 (1993).

F. Hutchinson, et al., Simple And Complex Cell Cycles, 5 Animal Review 341–95 (1989).

*Primary Examiner*—Lila Feisee
*Assistant Examiner*—John Lucas
*Attorney, Agent, or Firm*—Quarles & Brady

[57] ABSTRACT

A method of determining the proliferative status of a carcinoma is disclosed. One obtains a patient sample and then quantitatively analyzes the sample for NGAL gene expression product. The amount of NGAL expression product is compared with a standard curve to determine the S-phase value. The sample can be breast tissue or breast fluid aspirate. Alternatively, blood can by analyzed for this marker to diagnose metastasis.

4 Claims, No Drawings

IMMUNOHISTOCHEMICAL DETECTION ASSAY FOR CARCINOMA PROLIFERATIVE STATUS

CROSS-REFERENCE TO RELATED APPLICATIONS

This application is a continuation-in-part of U.S. Ser. No. 08/567,509, filed Dec. 5, 1995 now U.S. Pat. No. 5,627,034.

FEDERALLY SPONSORED RESEARCH

This invention was made with United States government support awarded by NIH, Grant # CA 58328. The United States government has certain rights in this invention.

BACKGROUND OF THE INVENTION

This invention relates to a method for determining carcinoma proliferative status. One examines breast carcinoma and adjacent tissue for NGAL protein using immunohistochemical staining techniques.

The oncogene c-erbB-2 is known to be associated with the clinical progression of human breast cancer. In vivo models utilizing c-erbB-2's rodent homolog, neu, have been developed to try to evaluate the role of c-erbB-2 in mammary carcinogenesis and tumor biology. In one model transgenic mice have been generated in which the expression of activated neu is targeted to the mammary gland using mammary-specific promoters. In a second model the activated neu oncogene has been directly and stably introduced into in situ rat mammary epithelial cells, using a replication-defective retroviral vector. With both methods, neu was found to be a potent tumor inducer.

We previously have reported "The isolation of a lipocalin uniquely overexpressed in neu-initiated rat mammary carcinomas". S. Stoesz et al., 1994 AACR Abstract. This lipocalin has been named "NRL" (for neu-related lipocalin). The disclosure of this abstract and of all other publications referred to herein are incorporated by reference as if fully set forth herein. As lipocalins are known to have a wide range of functions, the specific function of NRL is not known.

A protein somewhat homologous to rat NRL, human NGAL, has been isolated and sequenced. Various CDNA gene sequences coding for NGAL and NGAL's protein sequence have been reported in L. Kjeldsen et al., *J. Biol. Chem.* 268:10425–10432 (1993); J. Bundgaard et al., *Biochem. Biophys. Res. Comm.* 202[3]:1468–1475 (1994); S. Bartsch et al., *FEBS Let.* 37:255–289 (1995). NGAL (also known as human neutrophil lipocalin/HNL) has been found in a variety of cell types (e.g. bone marrow; ovarian cell cancers). Again, its specific function is not known. Note that Bundgaard reported the first base of the mature protein as Q from CAG, whereas Kjeldsen at one location reported an E at that position. The present claims use "NGAL" to cover both variants.

Treatment and diagnosis of breast carcinoma can be improved by a precise determination of the proliferative status of the cancer. One important measure of proliferative status is the percentage of cells in "S-phase". S-phase is the phase of the cell cycle in which duplication of DNA occurs. See generally F. Cross et al., *Annu. Rev. Cell Biol.* 5:341–395 (1989). Measurement of the percentage of cells in a biopsy sample that are in S-phase is an indicator of cellular proliferation status. A high percentage of cells in S-phase is known to be indicative of a poor prognosis for tumors, absent very aggressive treatment.

The percentage of carcinoma cells in S-phase has been measured by cell staining, flow cytometry, and by analyzing certain markers. Known techniques have problems (e.g. high cost; time consuming) and specific equipment requirements that make the techniques unattractive for routine clinical laboratory usage. Thus, a need exists for an improved assay to determine the proliferative status of carcinomas.

BRIEF SUMMARY OF THE INVENTION

In one aspect, the invention provides a method of determining the relative degree of proliferation of a human breast carcinoma. One obtains a sample of the carcinoma. One then uses an antibody having specificity for NGAL protein to bind to NGAL protein in the sample. One then uses a marker bound to the antibody to mark the extent to which NGAL protein is present in the carcinoma. NGAL protein, as used herein, is a protein having at least SEQ ID No. 1 sequences 21–197.

In a preferred form the sample also has tissue adjacent the carcinoma. The marker then also marks the extent to which NGAL protein is present in the adjacent tissue.

In one aspect the method is an immunohistochemical staining assay where the marker creates a visible color to mark the presence of the NGAL.

It will be appreciated that one object of the present invention is to provide an assay for cancer proliferation in breast tissue.

Another object of the present invention is to provide a technique to minimize false positives by also analyzing surrounding tissues for NGAL.

Other objects, features and advantages of the present invention will become apparent after examination of the specification and claims which follow.

DETAILED DESCRIPTION OF THE INVENTION

A standard curve can be created by determining S-phase values via flow cytometry for a panel of human mammary tumor cells, then determining NGAL protein levels for those same known samples using, for example, the NGAL protein assay of S. Xu et al., *J. Immunol. Meth.* 171:245–252 (1994). We have found that NGAL protein levels in carcinomas are predictive of S-phase values. Immunohistochemical stain "standards" can then be developed for these knowns.

Obtaining Human Samples For Initial Correlation Studies

Human female breast tissues suspected of harboring a carcinoma were obtained by standard biopsy methods known to one of skill in the art. For example, aspiration (or fine needle) biopsy, which involves the aspiration of cells and tissue fragments through a needle that has been guided into the suspect tissue, was used.

Needle (or core) biopsy, which involves obtaining a core of tissue through a specially designed needle introduced into the suspect tissue, is another option. Incisional biopsies, which involve the removal of a small wedge of tissue from a larger tumor mass, and excisional biopsies, which involve an excision of the entire suspected tumor tissue with little or no margin of surrounding normal tissue, are other examples of suitable tissue extraction methods to confirm the correlation with S-phase. See generally V. DeVita, Jr. et al., *Cancer Principles and Practice of Oncology* Vol. 1, 4th Ed., J.B. Lippincott Co., pp. 243–244 (1993).

Tissue may be prepared as follows for protein analysis. In order to extract protein, tissue can be homogenized with a Polytron in PBSTDS (10 mM sodium phosphate, dibasic;

154 mM sodium chloride; 12 mM deoxycholic acid, sodium salt; 1 mM sodium fluoride; 3.5 mM sodium dodecyl sulfate (SDS); 31 mM sodium azide; 1% Triton X-100; 1 mM phenylmethylsulfonyl fluoride) at a concentration of 100 mg per ml, and centrifuged at 10,000 g for 15 min at 4° C. One then removes the supernatant containing the soluble protein.

Assay

We examined patient tissue from a mammary carcinoma for the absolute amount of the NGAL protein. This examination was done via an RIA. See e.g. S. Xu et al., *J. Immunol. Meth.* 171:245–252 (1994). It can also be done via an enzyme-linked immunosorbent assay (ELISA) reaction. In an ELISA, one exposes the sample to an antibody specific for NGAL. Polyclonal anti-serum to NGAL can be obtained from a rabbit that has been immunized with NGAL. After binding of the polyclonal antibody to NGAL protein, one exposes the mixture to a second antibody (e.g. goat anti-rabbit) that is linked to an enzyme color change label. Detection of this label indicates the presence of NGAL antigen.

More specifically, anti-NGAL (monoclonal or polyclonal) capture antibodies can be coated on microtiter plates. Following washes, patient samples containing unknown NGAL antigen concentration levels are incubated on the plates. After washing out unbound antigen, a secondary anti-NGAL antibody is added to the wells and incubated. This secondary antibody may be enzyme-labelled, or is followed with a tertiary enzyme-labelled antibody which recognizes the secondary, but not capture, antibodies. After unbound antibody is washed out, an appropriate chromogenic enzyme substrate is added to the wells. The degree of color change produced with the substrate's incubation is proportional to the concentration of NGAL derived protein in the tumor sample, and is compared to known concentration standards of recombinant NGAL run in parallel. See E. Engvall et al., *Immunochemistry* 8:871–879 (1971) for general ELISA techniques.

From an examination of the ELISA results, one would be able to determine the level of NGAL protein present in patient tissue samples and compare this to a tumor panel with known prognostic and S-phase histories. One could also use other methods, such as Western blots, to analyze the amount of NGAL protein in a sample.

Known Human Breast Tumor Samples

We examined tissue from 15 random human breast tumors with known S-phase percentages (the S-phase percentages were reported to us by others). We found that four samples indicated the presence of high levels of NGAL expression product. The results are tabulated below in Table 2.

TABLE 2

| TUMOR | NGAL | S-PHASE (%) |
|---|---|---|
| 1 | – | 3.2 |
| 2 | – | 3.1 |
| 3 | – | 3.7 |
| 4 | – | 1.1 |
| 5 | ++ | 22.3 |
| 6 | – | 1.6 |
| 7 | – | 10.4 |
| 8 | – | 9.0 |
| 9 | ++ | 15.3 |
| 10 | + | 4.0 |
| 11 | – | 1.5 |

TABLE 2-continued

| TUMOR | NGAL | S-PHASE (%) |
|---|---|---|
| 12 | + | 14.6 |
| 13 | – | 8.2 |
| 14 | – | 1.6 |
| 15 | – | 5.5 |

A symbol of + or ++ indicates that expressed, or strongly expressed, respectively, NGAL expression product was detected. Statistical analysis shows the S-phase association with NGAL to be p=0.0051.

Polyclonal Antibody Generation And Purification

Three pathogen-free New Zealand white rabbits (Hazelton, Kalamazoo, Mich.) were initially immunized with 400 µg purified NGAL recombinant protein. The protein was emulsified in an equal volume of complete Freund's adjuvant (Sigma, St. Louis, Mo.), using 2 syringes connected through a luer fitting. The mixture was administered intradermally in 10–20 sites. In four 4-week increments booster injections were given subcutaneously, using 100–300 µg protein diluted in Dulbecco's phosphate-buffered saline (D-PBS) (Life Technologies, Gaithersburg, Md.) and emulsified in incomplete Freund's adjuvant (Sigma). Thirty ml whole blood was collected 12 days following boosts, clotted and centrifuged at 3000 g for 15 min at 4° C., and antiserum frozen at –80° C. Relative antibody production, specificity and background were determined by indirect enzyme-linked immunosorbent assay (ELISA) (Pierce), using bovine serum albumin and preimmune rabbit serum as negative controls.

An affinity column was constructed using the AminoLink immobilization kit (Pierce) and 3 mg purified recombinant NGAL that had previously been concentrated to 0.5 ml with a Centriplus concentrator, 10 kD cutoff (Amicon, Beverly, Mass.). Eight mg of IgG, purified from antiserum using a HiTrap 1 ml Protein A column (Pharmacia Biotech) was loaded and washed on the affinity column with 50 mM Tris, pH 7.5, and eluted with 0.1 M Glycine-HCl, pH 2.9. Column fractions were monitored for peak IgG by absorbance at 280 nm.

Immunohistochemistry

Fresh tissues for immunohistochemistry were obtained from breast biopsy specimens and a small sample of tumor tissue and adjacent normal breast tissue was embedded in OCT compound (Miles, Elkhart, Ind.), snap-frozen and stored at –70° C. Five µm frozen sections were mounted on poly-L-lysine-coated slides and fixed in 70% ethanol for 5 minutes. Endogenous peroxidase activity was quenched with 3% $H_2O_2$ in methanol for 10 minutes. After blocking with Powerblock reagent (DAKO, Carpinteria, Calif.) for five minutes, slides were incubated with affinity-purified anti-NGAL rabbit polyclonal antibody at a concentration of 18 µg/ml. Pre-immune IgG at the same protein concentration was used as a negative control. Binding was visualized using the LSAB+ detection system (DAKO) and 3,3'-diaminobenzidine (DAB) peroxidase substrate. The degree of brown coloration was proportionate to NGAL concentration.

Alternatively, paraffin imbedded sections can be prepared. In some of our experiments, routinely processed paraffin blocks of breast carcinomas were obtained from the University of Wisconsin pathology archives. Such slides were dried in an oven (55°–60° C.) before being deparaffinized in several changes of xylene and hydrated through a series of graded alcohols to water. A known positive control was treated identically to the cases being studied. For antigen retrieval, slides underwent microwave treatment in 1 mM EDTA (pH 8.0) for 20 min., followed by a 20 min. cool-down under running water. Slides were then bar-coded and placed in 1×APK wash solution (all equipment and reagents from Ventana Biotek Systems, Tucson, Ariz., unless stated otherwise).

The slides were then loaded onto an automated immunostainer (Ventana gen$^{II}$) for standardized incubation times and temperatures. Anti-NGAL affinity purified rabbit antiserum or pre-immune IgG as a negative control was used at a concentration of 1.75 μg/Ml for 30 min. at 37° C. The biotin-avidin-horseradish peroxidase method with diaminobenzidine substrate was employed for antigen detection. Slides were counterstained on the instrument with hematoxylin (Sigma, St. Louis, Mo.). All slides were removed from the stainer and rinsed in detergent water for removal of coverslip oil. The slides were then dehydrated through a series of graded alcohols and cleared in several changes of xylene before being coverslipped with a synthetic mounting medium.

NGAL Immunohistochemical Localization

Breast tumors showed high positive reactivity (brown stain) in the carcinomas, with little color outside thereof except in adjacent normal ducts. This confirmed that common inflammation unassociated with S-phase was not the cause of the NGAL.

UTILITY

The present invention is believed to be useful for medical screening and as a diagnostic tool. In that some existing biopsy procedures already involve creation of frozen or paraffin imbedded sections for analysis, the present invention can readily be implemented as an adjunct diagnostic tool.

It will be appreciated that the above preferred embodiments are merely examples of the invention. Many other variations are believed to be within the scope of the claims. For example, it has been determined by us that low NGAL levels also correlate with low levels of estrogen receptor protein and low levels of progesterone receptor protein. Using known estrogen/progesterone level samples (e.g. determined by known methods) one can readily create a standard cure for NGAL immunohistochemical assay versus estrogen/progesterone levels.

The present invention also provides a technique for checking false positives in other NGAL assays. In our tests, up to 4% of NGAL positives showed significant NGAL in tissue not associated with the carcinoma.

Thus, the claims should be looked to in order to judge the full scope of the invention.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 197 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met Pro Leu Gly Leu Leu Trp Leu Pro Ser Leu Leu Gly Ala Leu His
  1               5                  10                  15

Ala Gln Ala Gln Asp Ser Thr Ser Asp Leu Ile Pro Ala Pro Pro Leu
             20                  25                  30

Ser Lys Val Pro Leu Gln Gln Asn Phe Gln Asp Asn Gln Phe Gln Gly
         35                  40                  45

Lys Trp Tyr Val Val Gly Leu Ala Gly Asn Ala Ile Leu Arg Glu Asp
     50                  55                  60

Lys Asp Pro Gln Lys Met Tyr Ala Thr Ile Tyr Glu Leu Lys Glu Asp
 65                  70                  75                  80

Lys Ser Tyr Asn Val Thr Ser Val Leu Phe Arg Lys Lys Lys Cys Asp
                 85                  90                  95

Tyr Trp Ile Arg Thr Phe Val Pro Gly Cys Gln Pro Gly Glu Phe Thr
                100                 105                 110

Leu Gly Asn Ile Lys Ser Tyr Pro Gly Leu Thr Ser Tyr Leu Val Arg
             115                 120                 125
```

| | | | | | | | | | | | | | | |
|---|---|---|---|---|---|---|---|---|---|---|---|---|---|---|
| Val | Val<br>130 | Ser | Thr | Asn | Tyr | Asn<br>135 | Gln | His | Ala | Met | Val<br>140 | Phe | Phe | Lys | Lys |
| Val<br>145 | Ser | Gln | Asn | Arg | Glu<br>150 | Tyr | Phe | Lys | Ile | Thr<br>155 | Leu | Tyr | Gly | Arg | Thr<br>160 |
| Lys | Glu | Leu | Thr | Ser<br>165 | Glu | Leu | Lys | Glu | Asn<br>170 | Phe | Ile | Arg | Phe | Ser<br>175 | Lys |
| Ser | Leu | Gly | Leu<br>180 | Pro | Glu | Asn | His | Ile<br>185 | Val | Phe | Pro | Val | Pro<br>190 | Ile | Asp |
| Gln | Cys | Ile<br>195 | Asp | Gly | | | | | | | | | | | |

We claim:

1. A method of determining the relative degree of proliferation of a human breast carcinoma, comprising:
    (a) obtaining a sample of the carcinoma;
    (b) using an antibody having specificity for NGAL protein to bind to NGAL protein in the sample;
    (c) using a marker bound to the antibody to indicate the extent to which NGAL protein is present in the carcinoma.

2. The method of claim 1, wherein the sample also has tissue adjacent to the carcinoma and the marker also indicates the extent to which NGAL protein is present in the adjacent tissue.

3. The method of claim 2, wherein the method is an immunohistochemical staining assay in which the sample is a section and the marker creates a visible color that indicates the presence of NGAL protein.

4. The method of claim 1, further comprising the step of using the extent to which NGAL protein is present in the carcinoma to determine the extent to which estrogen receptor protein and progesterone receptor protein are present in the carcinoma.

* * * * *